(12) United States Patent
Knodel et al.

(10) Patent No.: US 8,114,118 B2
(45) Date of Patent: Feb. 14, 2012

(54) MEDICAL INSTRUMENT

(75) Inventors: Frank Knodel, Knittlingen (DE); Stephan Prestel, Rheinstetten-Mörsch (DE); Carl-Sebastian Wagner, Bretten (DE); Josef Bartolic, Karlsruhe (DE)

(73) Assignee: Richard Wolf GmbH, Knittlingen (DE)

( * ) Notice: Subject to any disclaimer, the term of this patent is extended or adjusted under 35 U.S.C. 154(b) by 1543 days.

(21) Appl. No.: 11/005,145

(22) Filed: Dec. 6, 2004

(65) Prior Publication Data

US 2005/0125027 A1     Jun. 9, 2005

(30) Foreign Application Priority Data

Dec. 6, 2003  (DE) .................................. 103 57 105

(51) Int. Cl.
*A61F 17/00* (2006.01)
*B25G 3/02* (2006.01)
*B23B 31/02* (2006.01)
(52) U.S. Cl. ............. 606/205; 279/75; 279/82; 279/125
(58) Field of Classification Search .................. 606/205; 279/29, 30, 74, 75, 82, 904–906, 125, 157
See application file for complete search history.

(56) References Cited

U.S. PATENT DOCUMENTS

| 4,577,875 A * | 3/1986 | Miyakawa ...................... 279/75 |
| 6,358,267 B1 | 3/2002 | Murakami et al. |
| 2001/0017447 A1* | 8/2001 | Baumann et al. ............ 279/19.4 |

FOREIGN PATENT DOCUMENTS

| DE | 43 41 736 A1 | 6/1995 |
| DE | 198 09 120 C1 | 8/1999 |

OTHER PUBLICATIONS

Machine translation of Kupferschmid (DE 198 09 120) retrieved from European Patent Office website in May 2010.*

* cited by examiner

*Primary Examiner* — Gary Jackson
*Assistant Examiner* — Eric Blatt
(74) *Attorney, Agent, or Firm* — Panitch Schwarze Belisario & Nadel LLP

(57) ABSTRACT

A medical instrument has an instrument insert and an instrument handle, which are detachably connected to one another. An actuation rod of the instrument insert is releasably connectable to a movable grip of the instrument handle via a locking connection. A blocking element is provided which blocks the movable grip when the actuation rod has been released.

17 Claims, 5 Drawing Sheets

MEDICAL INSTRUMENT

BACKGROUND OF THE INVENTION

The invention relates to a medical instrument and in particular to a medical forceps.

A surgical tubular shank instrument is known for example from German Patent DE 198 09 120 C1, which comprises a grip part and a shank which is detachably connectable to the grip. An actuation rod is movably arranged in the shank in order to be able to move parts, for example a forceps jaw at the distal end of the shank, via a movable hand grip on the grip part. The shank and the actuation rod are connected via ball locking connections to the grip or to an actuation rod arranged in this. For complete connection of the shank and the actuation rod to the grip, two ball-locking connections thus need to be locked. The assembly is therefore awkward, and the user may not directly recognize whether both connections are securely locked and the functioning ability of the instrument is ensured.

BRIEF SUMMARY OF THE INVENTION

It is therefore an object of the invention to provide an improved medical instrument which permits a simpler connection of an instrument insert to an instrument handle, and with which the user may easily recognize the operational readiness of the instrument.

The medical instrument according to the invention, for example a medical forceps, comprises an instrument insert and an instrument handle, which are detachably connected to one another. The detachability permits the exchange of instrument inserts so that various instruments inserts may be combined with one and the same instrument handle. Furthermore, for overhaul or cleaning the instrument insert may be easily separated from the instrument handle, which may then continue to be used with another instrument insert.

An actuation rod for moving elements at the distal end of the instrument insert, for example a forceps jaw, may be arranged inside the instrument insert. The actuation rod may be detachably connected to a movable grip of the instrument handle via a locking connection. In the connected condition, the actuation rod transmits a movement of the grip onto the elements which are to be moved at the distal end of the instrument insert.

According to the invention, a blocking element is provided which blocks the movable grip when the actuation rod has been detached. This arrangement has the advantage that the movable grip, when detached from an instrument insert, is held in a defined location, so that it may be connected to an actuation rod again in a simple and secure manner when an instrument insert is attached onto the instrument handle. Therefore, one does not need to take care that the grip is located in a certain position in order to be able to be connected to the actuation rod, as is the case with instruments known from the prior art (see, e.g., German Patent DE 198 09 120 C1). According to the invention, the grip is automatically held by the blocking element in that position in which it may be connected to the actuation rod.

Furthermore, the blocking element is designed such that when the actuation rod has been correctly connected, it may release the grip again. Thus, for the user it is ensured that whenever the grip may be moved, the instrument insert is correctly connected to the instrument handle and complete operational capability of the instrument is given. In this manner, a very simple handling of the instrument according to the invention is achieved. The instrument insert and the instrument handle need only be put together without having to more closely observe a predefined setting or positioning of individual elements.

Preferably, a receiver connected to the movable grip is arranged in the instrument handle, for connection to the proximal end of the actuation rod. The blocking element is arranged on the receiver and may be moved by a spring element into a blocking position and by the proximal end of the actuation rod against the spring force of the spring element into a released position. The spring element thus has the effect that the blocking element is designed in a self-blocking manner, i.e., on removal of the actuation rod from the receiver, the grip blocks automatically, preferably in a predefined position, so that the grip may not be moved when the actuation rod is released. The receiver for the actuation rod is thereby also held in a predefined position, so that the actuation rod may be easily connected again to the receiver.

Because the blocking element is moved back into the released position upon insertion of the actuation rod, the blocking element on attaching the instrument insert onto the instrument handle is automatically released again when the actuation rod is inserted into the receiver. If the actuation rod is again connected to the receiver, the user may thus move the grip again, and the correct functioning of the instrument is ensured. The connection between the receiver and the proximal end of the actuation rod is preferably designed such that the actuation rod may only be removed from the receiver when the receiver is located in a predefined position in which then the receiver and the movable grip are fixed when the actuation rod has been removed.

The locking connection between the actuation rod and the movable grip is further preferably designed as a ball locking connection. Such a connection permits a simple assembly of the actuation rod and the grip or of the actuation rod and the receiver which is connected to the grip.

For this purpose, an annular groove is preferably formed at the proximal end of the actuation rod, and the receiver is designed as a cylinder sleeve into which the proximal end of the actuation rod may be inserted. The cylinder sleeve has at least one locking ball arranged therein, which may engage with the annular groove. This design of the engagement elements, i.e., the annular groove and the locking ball, permits the locking ball to engage with the annular groove in each and every peripheral position. On the one hand, this design has the advantage that on assembling the instrument one does not have to take care with regard to a certain angular position between the instrument insert and the instrument handle or between the actuation rod and the receiver. On the other hand, this design permits the possibility of rotating the instrument insert with respect to the instrument handle, for example in order to be able to bring a forceps jaw arranged at the distal end of the instrument insert into a desired angular position during an operation.

The locking ball is usefully arranged in a through-bore in the wall of the cylinder sleeve in a direction transverse to the longitudinal axis of the cylinder sleeve, wherein the locking ball has a diameter which is larger than the thickness of the wall. This means the locking ball projects either beyond the inner periphery of the cylinder sleeve or beyond the outer periphery of the cylinder sleeve. The actuation rod is inserted into the cylinder sleeve in the longitudinal direction of this sleeve, i.e., the locking ball may be moved transversely to the insertion direction of the actuation rod. The actuation rod has at its proximal end an outer diameter which corresponds essentially to the inner diameter of the cylinder sleeve, so that the locking ball, when it projects inwardly into the cylinder sleeve, may engage into the annular groove at the proximal end of the actuation rod and may thus fix the actuation rod in the cylinder sleeve. In order to disengage the actuation rod from the cylinder sleeve, the locking ball must be moved radially outwardly so that it projects outwardly on the outer periphery of the cylinder sleeve.

In order to permit this, a recess or shoulder is provided on a guide in which the cylinder sleeve is movably guided. The locking ball may engage with this shoulder or recess in order to disengage the locking ball from the actuation rod and to simultaneously block the cylinder sleeve in the guide. The cylinder sleeve is movable in the guide in its longitudinal direction, i.e., also in the longitudinal and movement direction of the actuation rod, in order to transmit as movement of the movable grip onto the actuation rod. A recess or shoulder is provided at a defined position in the guide, and the guide radially widens at this recess or shoulder. At this location the locking ball may exit radially outwardly from the through-bore, so that inside the cylinder sleeve the ball may disengage from the annular groove at the proximal end of the actuation rod. Thus, the actuation rod is released and may be removed from the cylinder sleeve.

Since the locking ball at the outer periphery of the cylinder sleeve simultaneously enters into the recess in the guide or bears on the shoulder in the guide, the cylinder sleeve is thereby blocked in the guide, i.e., it is firmly held in the given position, so that the grip is also blocked in this position. The recess or the shoulder in the guide is usefully positioned such that with movement of the cylinder sleeve is possible on operation. This movement is limited by the maximum linear displacement of the actuation rod. For example, for opening and closing a forceps jaw at the distal end of the instrument insert, the locking ball in the cylinder sleeve does not reach the position of the shoulder or recess in the guide and thus may not engage with the recess or shoulder. It is thereby ensured that the actuation rod always remains secured in the cylinder sleeve during operation.

For removal of the actuation rod, the instrument insert must first be moved by a predefined amount relative to the instrument handle, preferably in the longitudinal direction of the instrument insert away from the instrument handle. The actuation rod together with the cylinder sleeve is first moved relative to its guide until the cylinder sleeve in the guide reaches a position which it does not reach in normal operation and at which the locking ball may engage with the recess or widening in the guide. With a further movement of the actuation rod, the locking ball may thus disengage from the annular groove, so that the actuation rod as described is released inside the cylinder sleeve.

In this manner, it is ensured that on removal of the actuation rod, the movable grip and the receiver connected to it are first moved into a predefined coupling position at which the actuation rod may be coupled to the movable parts in the instrument handle on inserting the instrument insert. Because the locking ball is provided for securing the actuation rod as well as for blocking the movable parts in the instrument handle, it is ensured that whenever the handle is released, the movable receiver is always blocked in the instrument handle and vice versa. Thus, a self-securing connection may be created in a very simple manner, which securely rules out any maloperation.

Furthermore, the blocking element is preferably arranged inside the cylinder sleeve and in its blocking position maintains the engagement of the locking ball with the recess or shoulder in the guide, and in its released position releases the locking ball. The blocking element is designed such that when the actuation rod is removed from the cylinder sleeve, the blocking element holds the locking ball in its radially outwardly disengaged position, in which the locking ball secures the cylinder sleeve on its guide. For this purpose, the blocking element may be, for example, a plunger which is movable inside the cylinder sleeve and which is pressed in a distal direction by a spring element. When the actuation rod is inserted into the cylinder sleeve or receiver, the proximal end face of the actuation rod presses the plunger in the proximal direction, so that the actuation rod may be inserted into the cylinder sleeve until the annular groove on the actuation rod comes into engagement with the locking ball. When the actuation rod is removed from the cylinder sleeve, the spring element presses the plunger in the distal direction to such an extent that it comes into the region of the cylinder sleeve in which the locking ball is arranged. At the same time, the plunger bears essentially on the inner wall of the cylinder sleeve, so that the locking ball may not enter into the inside of the cylinder sleeve, but is deflected radially outwardly and is held in the recess or on the shoulder of the guide of the cylinder sleeve.

According to a further preferred embodiment, the instrument insert comprises an instrument shank whose proximal end is designed as a Luer connection, which serves for connecting to the instrument handle and for connecting to a flexible tubing conduit. This design has the advantage that the proximal end of the instrument shank may be easily connected to common flexible tubing conduits for rinsing. No additional cleaning adapters are required as is usually the case with known instruments. Thus the instrument according to the invention demands no loose additional parts which are merely required for cleaning and may easily become lost. The Luer connection preferably serves simultaneously for centering the instrument shank on the instrument handle. For this purpose, the Luer connection is inserted into a cylindrical recess on the instrument handle in the longitudinal direction of the instrument shank, whereby the outer periphery of the Luer connection comes to bear on the inner wall of the cylindrical recess.

Furthermore, the instrument insert preferably comprises an instrument shank, which may be detachably connected to the instrument handle via a locking connection. This permits the complete instrument insert to be connectable to the instrument handle in a simple manner by locking, and likewise to be easily detached from the instrument handle again. Thus, the exchangeability of the instrument shank is possible without any problem. Preferably, the interface between the instrument shank and the instrument handle is designed such that different instrument inserts may be connected to one and the same instrument handle.

According to a first preferred embodiment, the locking connection between the instrument shank and the instrument handle comprises a locking bolt which is arranged on the instrument handle, is movable transversely to the longitudinal axis of the instrument shank and may releasably engage with a recess at the proximal end of the instrument shank. The locking bolt for this is preferably biased by a spring element in a manner such that it automatically engages into the recess at the proximal end of the instrument shank in order to secure the instrument shank on the instrument handle. For release, a push surface is provided on the locking bolt by which the user may push the locking bolt into a released position against the spring force of the spring element, in order to disengage the locking bolt from the instrument shank, so that this instrument shank may be removed from the instrument handle.

Preferably, the locking bolt engages at the same time behind the protrusions of the Luer connection. One therefore requires no additional engagement elements at the proximal end of the forceps shank. Furthermore, the protrusions of the Luer connection are designed as a peripheral annular projection, so that the locking bolt may engage behind the protrusion of the Luer connection at every angular position of the instrument shank with respect to its longitudinal axis. Thus, on the one hand, one does not need to respect a certain angular position on inserting the instrument shank, so that the insertion is simplified. On the other hand, the instrument may be designed such that on operation, the instrument shank and the instrument insert with it are also rotatable about the longitudinal axis of the instrument shank relative to the instrument handle, for example in order to be able to bring a forceps jaw at the distal end of the instrument insert into the desired position. Since the recess at the proximal end of the instrument shank, preferably formed by the Luer connection, is rotationally symmetrical, the locking connection between the instrument shank and the instrument handle does not have to be released for this.

According to a further preferred embodiment, the locking connection between the instrument shank and the instrument handle is designed as a ball locking connection. The ball locking connection permits a particularly compact construction of the locking connection and simultaneously a smooth and secure connection between the instrument shank and the instrument handle.

The ball locking connection between the instrument shank and the instrument handle preferably comprises a closure element for securing the ball locking connection and a grip element. The closure element may be moved into an unsecured position by movement of the grip element as well as independently of movement of the grip element. For detaching the instrument shank from the instrument handle, this arrangement permits the grip element to be moved in order to bring the closure element into an unsecured position in which the instrument shank may be removed from the instrument handle. Because the closure element may additionally be moved independently of the grip element, it is thus not necessary to move the grip element on assembling the instrument shank and the instrument handle.

Rather, on assembling the instrument, the grip element remains in a certain position, so that a user may firmly hold the respective instrument part (e.g., the instrument handle) at the grip element and put this together with the other instrument part, depending on whether the grip element and closure element are attached on an instrument handle or on the instrument shank. On assembling the instrument shank and the instrument handle, the closure element is merely moved over the counter-piece to be connected and does not need to be moved manually into the unsecured position by moving the grip. This means that when the closure element is arranged on the instrument handle, the closure element is moved into its unsecured position by inserting the instrument shank. Reversely, for the case that the closure element is arranged on the instrument shank, the closure element may be moved into its unsecured position by a corresponding part on the instrument handle when both parts are joined together.

Furthermore, the ball locking connection between the instrument shank and the instrument handle preferably comprises a closure sleeve for securing the ball locking connection, and a grip sleeve. The closure sleeve in a secured position blocks the movement of at least one locking ball and in an unsecured position frees the locking ball. The closure sleeve may be moved into the unsecured position by moving the grip sleeve as well as independently of movement of the grip sleeve. Locking balls are provided, for example, on the instrument shank and may engage with corresponding recesses, preferably an annular groove, on an element of the instrument handle for securing the instrument shank on the instrument handle. When the locking balls are engaged with the annular groove, they are secured in this position by the closure sleeve, so that they may not become disengaged from the recesses or the groove.

For release, the closure sleeve must be moved away from the locking balls, so that these may exit from the recesses or from the groove and may release the corresponding element. For this purpose, the closure sleeve may be moved via the grip sleeve into a released or unsecured position. To bring the locking balls into engagement with the groove again, when the instrument shank has been attached onto the instrument handle, the locking sleeve must first also be moved into the unsecured position, so that the balls may engage with the groove. For this purpose, the closure sleeve is designed such that it may move into the unsecured position independently of the grip sleeve, wherein the grip sleeve remains in its original position. This design allows the instrument to be held firmly at the grip sleeve on assembly without the grip sleeve having to move. The assembly of the instrument is considerably simplified by this design.

Preferably, the closure sleeve is arranged inside the grip sleeve and is held in the secured position by a spring element. The closure sleeve comprises at least one contact shoulder behind which a contact shoulder of the grip sleeve engages only in a direction which is opposite to the spring force of the spring element. The contact shoulder of the closure sleeve is preferably formed on its outer periphery, and the contact shoulder of the grip sleeve is preferably formed on its inner periphery. The rearward engagement of the closure sleeve by the grip sleeve only in the mentioned direction has the effect that the closure sleeve may be moved against the spring force of the spring element by movement of the grip sleeve.

On the other hand, the closure sleeve may also move independently of the grip sleeve against the spring force of the spring element, wherein the contact shoulders of the grip sleeve and the closure sleeve disengage. If only the closure sleeve is moved, the grip element is not, as a result, moved jointly. Furthermore, via the spring element and the closure sleeve as well as the contact shoulders, a force is exerted onto the grip sleeve, which ensures that the grip sleeve is likewise pressed into a predefined position by the spring element. The grip sleeve only needs to be moved together with the closure sleeve against the spring force for releasing the ball locking connection. On assembly of the instrument shank and the instrument handle, on account of a component to be inserted, only the closure sleeve is moved against the spring force, while the grip sleeve remains in its original position.

The closure sleeve and the grip sleeve are preferably movably guided on the instrument (e.g., forceps) handle, and the grip sleeve comes to bear on an abutment of the instrument handle when the closure sleeve is in its secured position. This means that the spring element, which presses the closure sleeve into its secured position, presses the grip sleeve against the abutment on the instrument handle via the contact shoulders between the closure sleeve and the grip sleeve. That is, the grip sleeve is likewise held in a predefined rest position via the spring element. Furthermore, the grip sleeve, when it is gripped, permits the instrument handle to be easily put together with the instrument shank, since the grip sleeve when it is moved in the connection direction, i.e., distally, comes to bear on the abutment and thus jointly moves the complete instrument handle.

If the grip sleeve and the closure element are provided on the instrument handle, the spring element is arranged such that it presses the closure sleeve in a distal direction into a secured position. Reversely, it is also possible to arrange the closure and grip sleeve at the proximal end of the instrument shank. In this case, the spring element presses the closure element in a proximal direction. The abutment between the grip element and the forceps shank is then also selected such that, by movement of the grip sleeve, the instrument shank may be moved in a proximal direction toward the instrument handle via the abutment.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
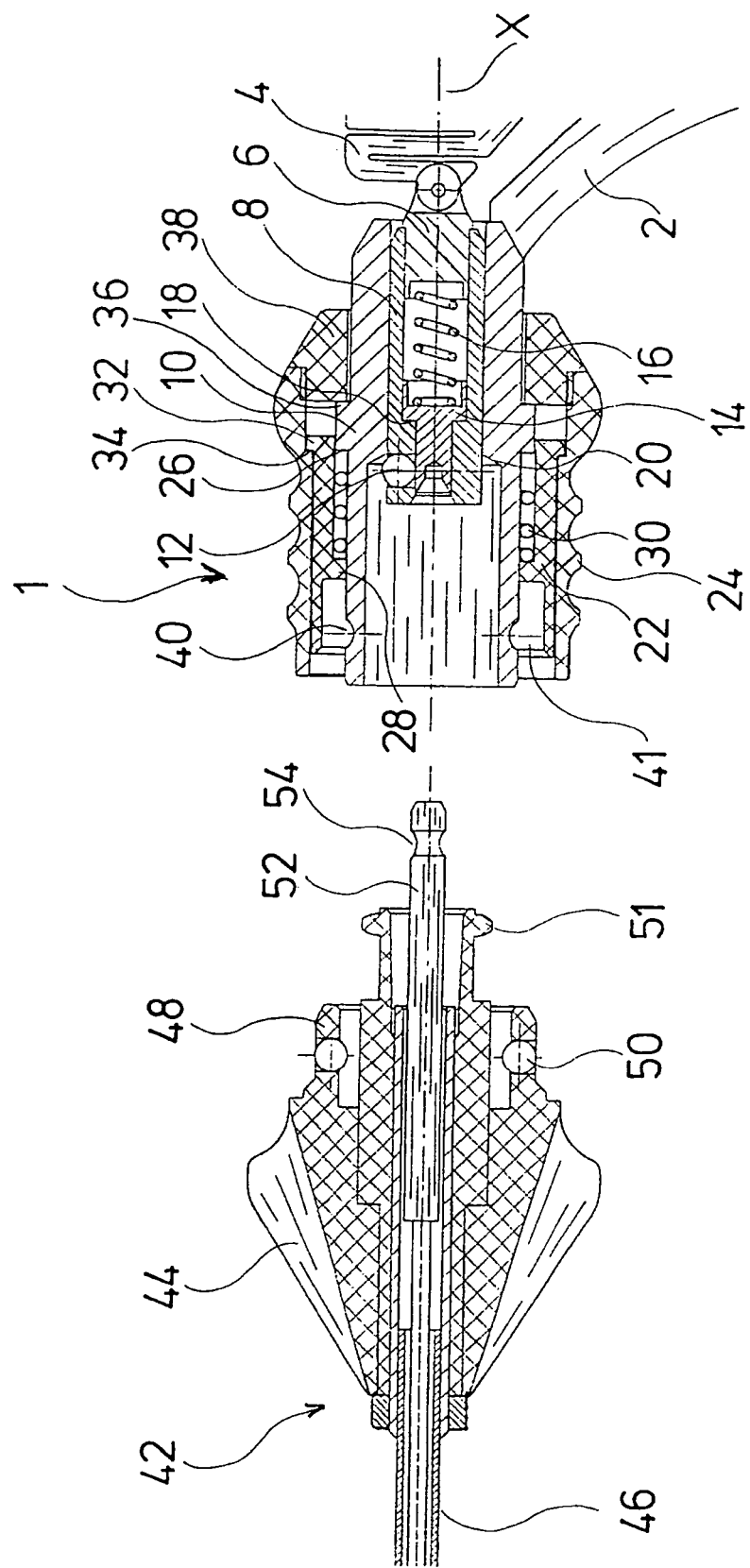
FIG. 1 is a sectioned view of the proximal end of an instrument insert and the distal end of an instrument handle according to a first embodiment of the invention, in a detached condition.
Figure 2:
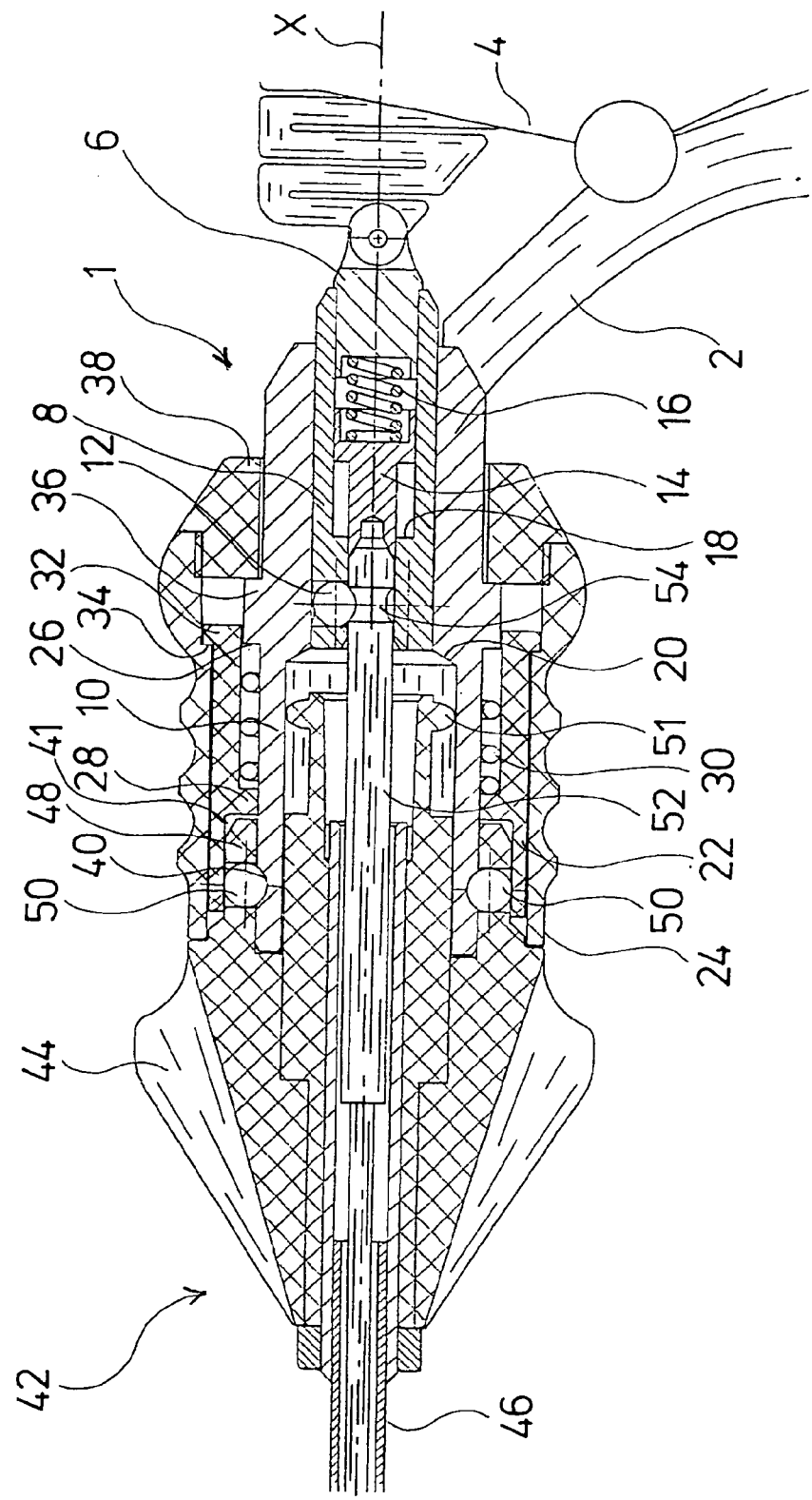
FIG. 2 is a sectioned view of the embodiment according to FIG. 1 in the assembled condition.

A first preferred embodiment of the invention is explained by way of FIGS. 1 and 2. FIG. 1 shows the distal end of an instrument handle 1, for example a forceps handle, as well as the proximal end of an instrument insert, for example a forceps insert, in section. The instrument handle comprises a fixed grip 2 and a movable grip 4 (both shown in fragment), with the movable grip being connected to a cylinder sleeve 8 via a connection part 6. The movable grip 4 is pivotally attached to the instrument handle 1, such that the movable grip 4 is movable along an arc extending tangentially to a longitudinal axis X of the instrument. The connection part 6 is firmly connected to the cylinder sleeve 8. The cylinder sleeve 8 is movably guided in the direction of the instrument longitudinal axis X in a cylinder receiver 10, which is firmly connected to the fixed grip 2. Radially outwardly directed through-bores are arranged in the region of the distal end of the cylinder sleeve 8, in which locking balls 12 are arranged. In the present case there are provided three through-bores distributed uniformly over the periphery of the cylinder sleeve 8, each bore containing one locking ball 12. The locking balls 12 have a diameter larger than the wall thickness of the cylinder sleeve 8, so that the locking balls in each case either protrude outwardly or inwardly on the cylinder sleeve.

A blocking element 14 in the form of a plunger is movably guided in the direction of the instrument longitudinal axis X inside the cylinder sleeve. The blocking element 14 is pressed distally against a shoulder 18 inside the cylinder sleeve 8 by a spring 16. The shoulder 18 is spaced a predetermined distance away from the locking balls 12. The distal end of the blocking element 14 in this position projects so far into the distal receiver region of the cylinder sleeve 8 that it covers the position of the locking balls 12 in the direction of the longitudinal axis X. At the same time, the blocking element 14 bears on the inner periphery of the cylinder sleeve 8 in a manner such that the locking balls 12 are pressed outwardly and protrude outwardly at the outer periphery of the cylinder sleeve 8. The locking balls 12 thereby come to bear on a contact shoulder 20 inside the cylinder receiver 10. The locking balls 12 at the same time lie on the distal side with respect to the contact shoulder 20, so that the cylinder sleeve 8 may not be moved proximally in the direction of the longitudinal axis X inside the cylinder receiver 10. The locking balls 12 thus hold the cylinder sleeve 8 firmly in the position shown in FIG. 1, in which the cylinder sleeve 8 and thus the movable grip 4 are blocked against a movement into the released condition.

Furthermore, a closure sleeve 22 and a grip sleeve 24 are arranged on the outer periphery of the cylinder receiver 10, wherein the closure sleeve 22 is arranged inside the grip sleeve 24 between the grip sleeve 24 and the outer periphery of the cylinder receiver 10. The closure sleeve 22 is guided on the outer periphery of the cylinder receiver 10 in the direction of the longitudinal axis X. At the same time, the cylinder receiver 10 comprises on its outer periphery a distally directed shoulder 26, and the closure sleeve 22 comprises a radially inwardly directed projection 28, which bears on the outer periphery of the cylinder receiver 10. A compression spring 30 in the form of a helical spring is arranged between the shoulder 26 and the projection 28, and this spring presses the closure sleeve 22 into the shown secured position.

The grip sleeve 24 is likewise guided in a movable manner in the direction of the longitudinal axis X on the outer periphery of the cylinder receiver 10. The closure sleeve 22 at its proximal end comprises an outwardly directed, annular projection 32, which with its distally directed side bears on a proximally directed shoulder 34 inside the grip sleeve 24. In the proximal direction the projection 32 does not engage with the grip sleeve 24, but is freely movable in the grip sleeve. This has the effect that the grip sleeve 24 via the projection 32 and the shoulder 34 is likewise pressed distally by the compression spring 30, but on movement of the closure sleeve 22 in the proximal direction is not however moved jointly. At the same time, an abutment is formed by an annular projection 36 on the outer periphery of the cylinder receiver 10, behind which the proximal end 38 of the grip sleeve 24 engages. In the region of the distal end of the cylinder receiver 10 on its outer periphery there is provided an annular groove 40, which is covered by the closure sleeve 22 in its secured position. The closure sleeve 22 is spaced from the annular groove 40 in the radial direction, so that an annular free space 41 is formed.

The instrument insert 42 at its proximal end comprises a rotation grip 44, which is firmly connected to the proximal end of the instrument shank 46, in order to be able to rotate the insert relative the instrument handle about the longitudinal axis X. In the region of its proximal end, the rotation grip 44 comprises a cylindrical engagement section 48, which may enter into the free space 41 between the closure sleeve 22 and the cylinder receiver 10 of the instrument handle from its distal side. Radially directed through-bores are provided in the engagement section 48, in which locking balls 50 are arranged. In the example shown there are provided three through-bores distributed uniformly over the periphery of the engagement section 48, with locking balls 50 therein. The locking balls 50 may engage with the annular groove 40 in order to secure the instrument insert 42 on the instrument handle 1. The proximal end of the forceps shank 46, which is arranged inside the engagement section 48 and projects proximally beyond this, is formed as a Luer connection 51, which may engage into the inside of the cylinder receiver 10 and comes to bear on the inner periphery. The instrument insert 42 is thereby centered in the instrument handle 1 with respect to the receiver. A rinsing conduit for flushing the instrument shank 46 may be very simply connected to the Luer connection 51 when the instrument insert 42 is separated from the instrument handle.

An actuation rod 52 is arranged inside the instrument shank 46 which extends in the direction of the longitudinal axis X to the distal end of the instrument insert 42, in order, for example, to move a forceps jaw which has not been shown here. The proximal end of the actuation rod 52 projects out of the proximal side of the Luer connection 51 and comprises a peripheral annular groove 54. The proximal end of the actuation rod 52 may furthermore be profiled, i.e., comprise planar side surfaces with an otherwise round cross section, in order to permit an improved rinsing ability of the instrument shank. The annular groove 54 may engage with the locking balls 12 in the cylinder sleeve 8 for locking the cylinder sleeve 8 on the actuation rod 52.

FIG. 2 shows a sectioned view of the arrangement according to FIG. 1 in the connected condition. For connecting the instrument insert 42 to the instrument handle 1, this handle is gripped at the grip sleeve 24 and/or the grips 2 and 4, while the instrument insert 42 is preferably gripped on the rotation grip 44. The instrument insert 42 and the instrument handle 1 are then moved together. If the grip sleeve 24 is gripped and is moved in the direction of the longitudinal axis X toward the instrument insert 42, the cylinder receiver 10 and thus the whole instrument handle 1 is likewise moved toward the instrument insert 42 via the projection 36. On joining together, the Luer connection 51 enters into the inside of the cylinder receiver 10. When the instrument insert 42 and the instrument receiver 1 are moved further together, the proximal end of the actuation rod 52 with the annular groove 54 enters into the inside of the cylinder sleeve 8. At the same time, the blocking element 14 is moved proximally against the spring force of the spring 16 until the annular groove 54 has reached a position in which the locking balls 12 may enter into the annular groove 54.

The actuation rod 52 is thereby connected to the cylinder sleeve 8 with a positive fit. At the same time, the locking balls 12 are disengaged from the contact shoulder 20, so that with a continued proximal movement of the instrument insert 42, the whole cylinder sleeve 8 is moved proximally. At the same time, the cylinder sleeve 8 enters so far into the proximal side of the cylinder receiver 10 that the radially directed through-bores with the locking balls 12 are directly covered by the inner wall of the cylinder receiver 10, whereby the locking balls 12 are held in engagement with the annular groove 54, so that the actuation rod 52 may no longer become disengaged from the cylinder sleeve 8 which is connected to the movable grip 4.

Simultaneously, on connecting the instrument handle 1 to the instrument insert 42, the engagement section 48 enters into the space 41 between the cylinder receiver 10 and the closure sleeve 22. At the same time, the locking balls 50 first abut on the distal end edge of the closure sleeve 22, which is then moved proximally against the spring force of the compression spring 30 to such an extent that the locking balls 50 come to lie over the annular groove 40 and may enter this groove. Since the closure sleeve 22 in the proximal direction does not come to bear on the grip sleeve 24, the grip sleeve 24 is not moved jointly with this movement of the closure sleeve 22, so that the grip sleeve 24 remains in its original position and may continue to be firmly held in order to lead the instrument handle and the instrument insert 42 together.

When the locking balls 50 engage into the annular groove 40, the locking balls 50 move radially inwardly in their through-bores in the engagement section 48, so that they may disengage from the end-face of the closure sleeve 22. At this point, the closure sleeve 22 is again moved distally by the compression spring 30 until the distal region of the closure sleeve 22 covers the through-bores in which the locking balls 50 are arranged. In this position the closure sleeve 22 prevents the locking balls 50 from moving radially outwardly and being disengaged from the annular groove 40. In this position the instrument shank 46 is thus secured on the instrument handle 1 by the closure sleeve 22.

Since the engagement elements are designed in the form of annular grooves 54 and 40 and locking balls 12 and 50, in the joined-together condition, the instrument insert 42 may be rotated relative to the instrument handle 1 about the longitudinal axis X by rotating at the rotation grip 44. By way of axial ribbing the annular groove 40 around its circumference, one may further provide a finely locking rotatability. Furthermore, on account of the rotationally symmetrical design of the parts engaging into one another, one does not have to respect a certain angular position of the instrument insert 42 relative to the instrument handle 1 on joining them together.

For releasing the connection between the instrument insert 42 and the instrument handle 1, the grip sleeve 24 is moved proximally in the direction of the longitudinal axis X, whereby the grip sleeve 24 via the shoulder 34 is engaged with the projection 32 of the closure sleeve 22, and the closure sleeve 22 is moved jointly in the proximal direction. When the closure sleeve 22 has been moved so far proximally by movement of the grip sleeve 24 that the closure sleeve 22 no longer covers the locking balls 50, and when the instrument insert 42 is moved distally relative to the instrument handle 1, the locking balls 50 may move radially outwardly and disengage from the annular groove 40.

When the instrument handle 1 and the instrument insert 42 are moved apart, the actuation rod 52 first remains engaged with the cylinder sleeve 8, so that the cylinder sleeve 8 is moved distally relative to the cylinder receiver 10, until the locking balls 12 exit from the proximal side of the cylinder receiver 10 and reach a position distally of the contact shoulder 20. In this position the locking balls 12 may move radially outwardly and disengage from the annular groove 54 so that the actuation rod 52 may be pulled distally out of the cylinder sleeve 8. At the same time, the blocking element 14 is pressed distally by the spring 16, whereby it bears with its end-face on the proximal end face of the actuation rod 52. At the same time, the blocking element 14 moves distally until it covers the through-holes with the locking balls 12 and thus secures the locking balls 12 in their radially outwardly deflected position in which they engage behind the contact shoulder 20. The blocking element 14 then comes to bear on the shoulder 18.

When the locking balls 12 engage behind the contact shoulder 20, the cylinder sleeve 8 is blocked in the cylinder receiver 10, so that the movable grip 4 may no longer be moved. In this manner, on the one hand, it is ensured that the movable grip 4 may only be moved if the instrument insert 42 is properly connected to the instrument handle 1. Furthermore, the connection of the instrument insert 42 and the instrument handle 1 is simplified, because the cylinder sleeve 8, which serves as a receiver for the actuation rod 52, is held in a defined position by the blocking on account of the locking balls 12.

Figure 3:
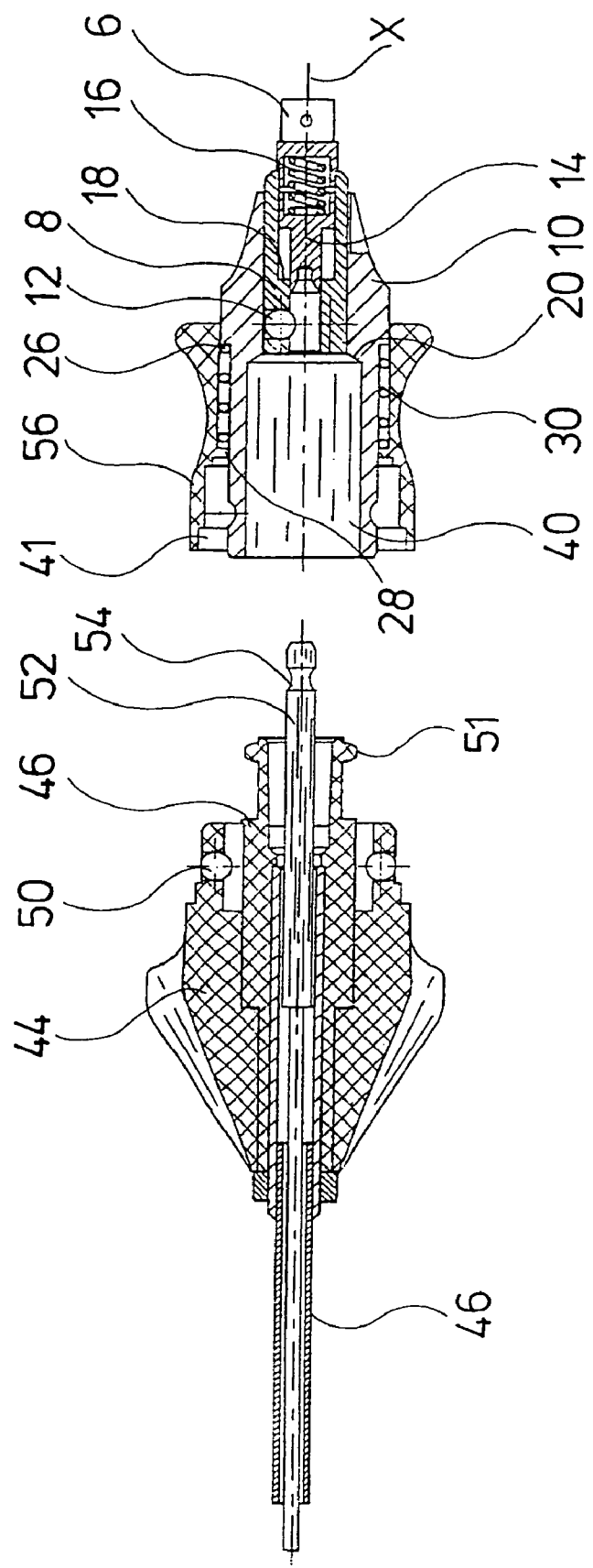
FIG. 3 is a sectioned view of the proximal end of an instrument insert and the distal end of an instrument handle according to a second embodiment of the invention, in a detached condition.

FIG. 3 shows an embodiment similar to the embodiment shown in FIG. 1, wherein here the closure sleeve 22 and the grip 24 are designed as a single piece grip 56. All remaining elements correspond to those elements described by way of FIGS. 1 and 2, so that the manner of functioning is also identical. The only difference in the functioning manner of the arrangement according to FIG. 3 to those previously described arrangements lies in the fact that with the embodiment according to FIG. 3, the grip sleeve 56, which unifies the elements of the grip sleeve 24 and the closure sleeve 22 according to the embodiments in FIGS. 1 and 2, likewise needs to be moved first distally in the direction of the longitudinal axis X, but then is moved proximally relative to the cylinder receiver 10 against the spring 30 in order to connect the instrument handle 1 to the instrument insert 42.

Figure 4:
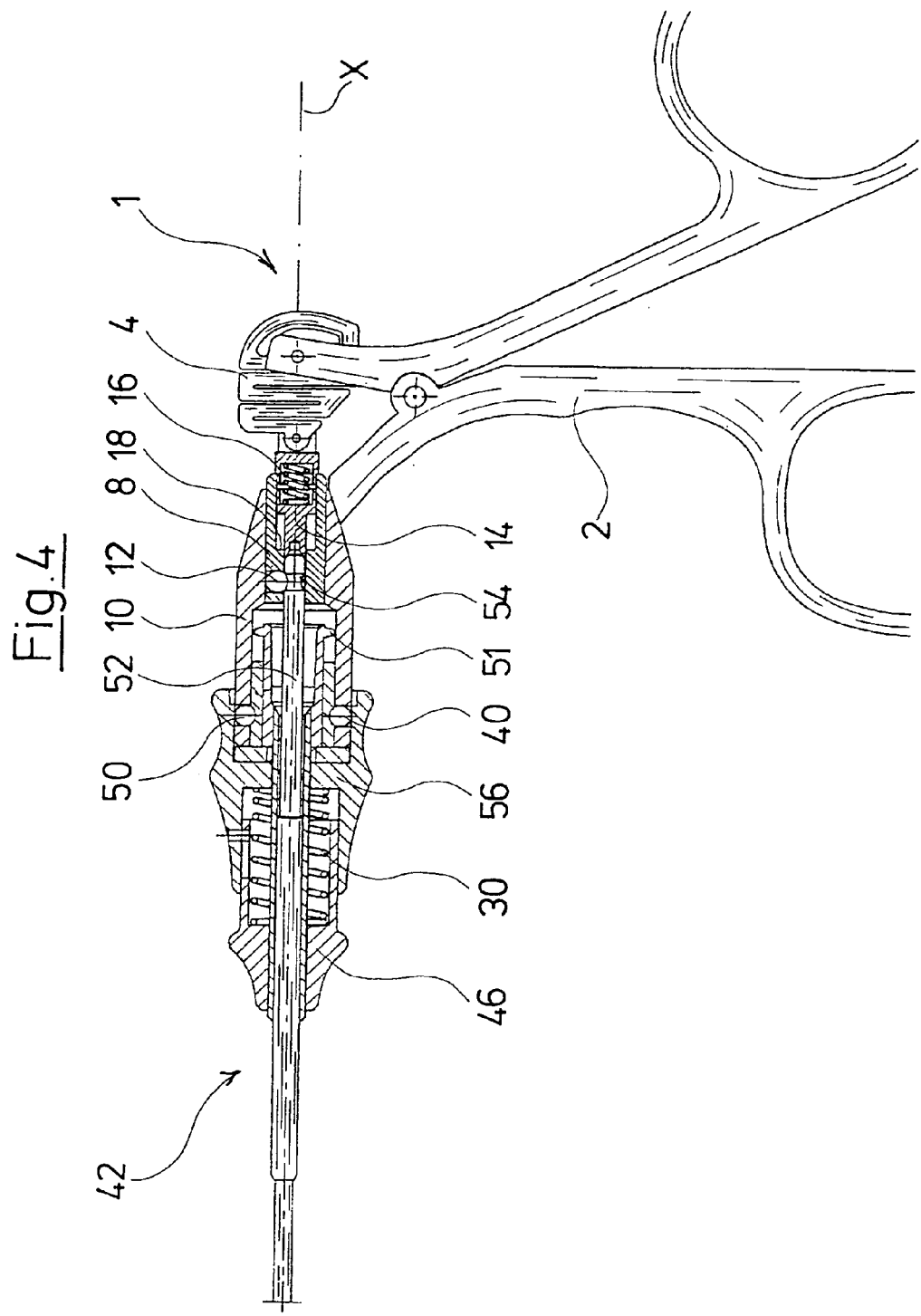
FIG. 4 is a sectioned view of an instrument handle with an attached instrument shank according to a third embodiment of the invention.

FIG. 4 in a sectioned view shows a further embodiment of the invention. The embodiment according to FIG. 4 also corresponds essentially to the previously described embodiments and in particular that embodiment described by way of FIG. 3. The difference of the third embodiment according to FIG. 4 from those previously described embodiments lies in the fact that with this embodiment, the locking balls 50 are arranged on sides of the instrument handle 1, and the annular groove 40 and the grip sleeve 56 are arranged on sides of the instrument insert 42. The manner of functioning however corresponds to the previous description. The blocking of the grips when the actuation rod 52 has been removed corresponds to the previously described embodiments. Such a reverse arrangement of the coupling elements on the instrument insert and handle is likewise possible with the embodiment with the closure sleeve 22.

Figure 5:
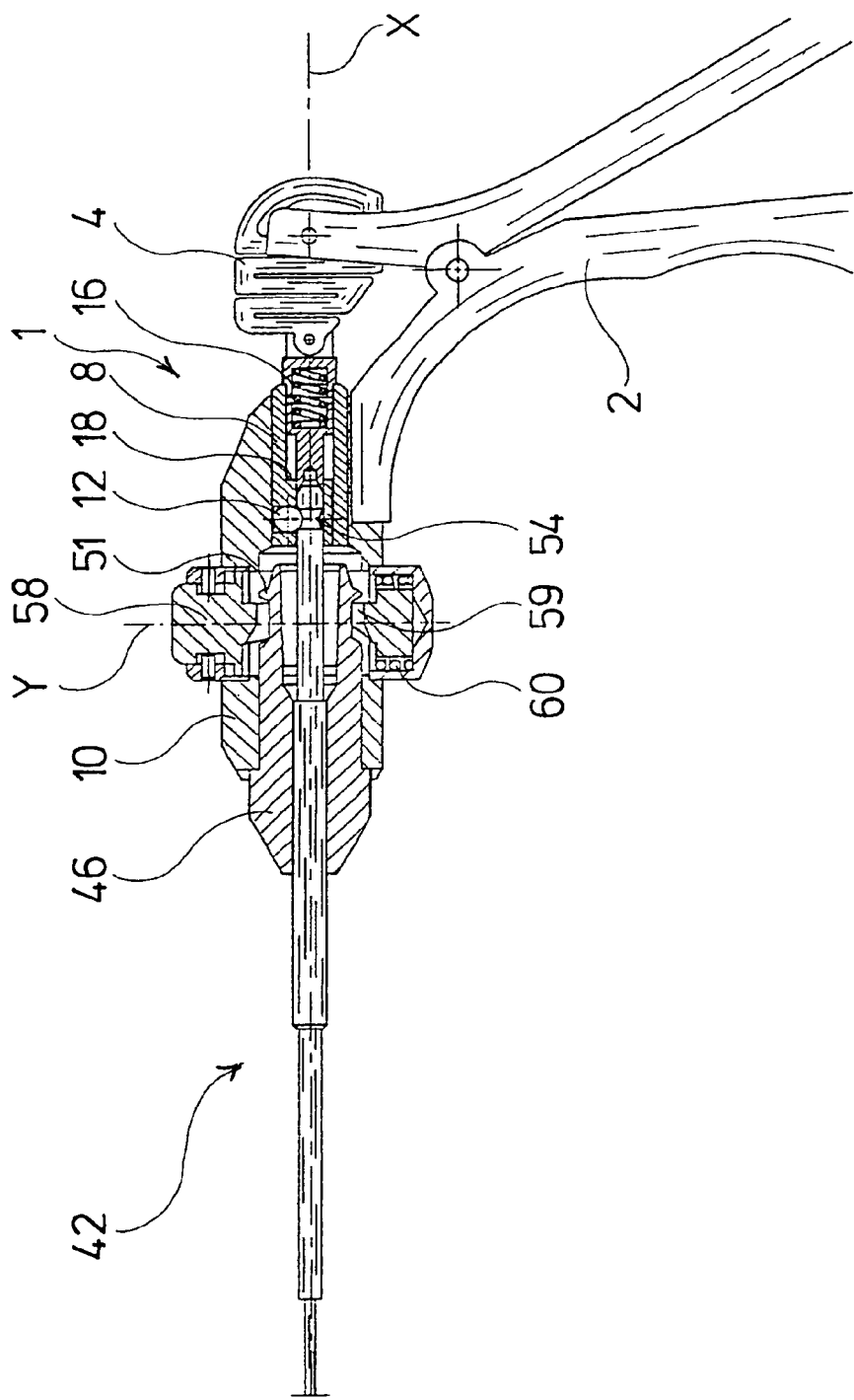
FIG. 5 is a sectioned view of an instrument handle with an attached instrument insert according to a fourth embodiment of the invention.

FIG. 5 shows a further embodiment, which differs from the previously described embodiments again only in the type of connection between the instrument insert 42 and the instrument handle 1. The manner of functioning of the blocking for the handle, when the actuation rod 52 has been removed, corresponds to the design described in detail by way of FIGS. 1 and 2. The connection between the instrument handle 1 and the instrument insert 42 or the proximal end of the instrument shank 46 is effected according to the embodiment in FIG. 5 by way of a locking bolt 58. The locking bolt 58 is arranged in the cylinder receiver 10 and extends transversely to the longitudinal axis X through the cylinder receiver 10, whereby it is movable in a direction of the axis Y normal to the longitudinal axis X. A through-hole 59 extends through the locking bolt in the direction of the longitudinal axis X transversely to the axis Y. The locking bolt 58 is pushed by way of a spring 60 in the direction of the axis Y into a closed position, in which the peripheral edges of the through hole 59 engage at least partly behind the radially outwardly protruding projection of the Luer connection 51. In this manner the instrument shank 46 is secured on the instrument handle 1 so that it may not be removed from the instrument handle 1 in the distal direction. For release, the locking bolt 58 is pressed manually against the spring force of the spring 60, so that the peripheral edge of the through-hole 59 is disengaged from the protrusion of the Luer connection 51, and the instrument shank 46 may be separated from the cylinder receiver 10 or from the instrument handle 1. The release and connection of the actuation rod 52 is effected with this embodiment just as described by way of FIGS. 1 and 2.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A medical instrument comprising an instrument insert (42) and an instrument handle (1) which are detachably connectable to one another, the instrument insert (42) having an actuation rod (52), the instrument handle (1) having a movable grip (4) and a receiver (10) connected to the movable grip (4), the receiver (10) adapted to receive a proximal end of the actuation rod (52) for connection thereto, the actuation rod (52) and the movable grip (4) being detachably connectable to one another via a locking connection (12, 54) such that movement of the movable grip moves the actuation rod along a longitudinal axis (X), a blocking element (14) preventing movement of the movable grip (4) along the longitudinal axis when the actuation rod (52) is detached, the movable grip being held in a defined location by the blocking element when the instrument handle is detached from the instrument insert, a cylinder sleeve (8) being arranged at least partially inside the receiver (10), the cylinder sleeve (8) being movable with respect to the receiver (10), the cylinder sleeve (8) having a longitudinal passageway extending completely therethrough, the passageway of the cylinder sleeve (8) receiving therein at least a portion of a connection part (6) connecting the moveable grip (4) with the cylinder sleeve (8), the blocking element (14) being arranged inside the cylinder sleeve (8) with a spring element (16), such that the blocking element (14) is urged into a blocking position by the spring element (16) and is urged into a released position by the proximal end of the actuation rod (52) against a spring force of the spring element (16).

2. The medical instrument according to claim 1, wherein the locking connection (12, 54) comprises a ball locking connection between the actuation rod (52) and the movable grip (4).

3. The medical instrument according to claim 1, wherein at least one locking ball (12) is movably arranged in a through-bore in a wall of the cylinder sleeve (8) in a direction transverse to the longitudinal axis (X) of the cylinder sleeve (8), and wherein the locking ball (12) has a diameter larger than a thickness of the wall.

4. The medical instrument according to claim 3, wherein the cylinder sleeve (8) is guided in the receiver (10), the receiver (10) having a recess or shoulder (20), and wherein the locking ball (12) is engageable with the recess or shoulder (20) to disengage the locking ball (12) from the actuation rod (52) and to simultaneously block the cylinder sleeve (8) in the receiver (10).

5. The medical instrument according to claim 4, wherein in its blocking position, the blocking element (14) holds the locking ball (12) engaged with the recess or shoulder (20) and in its released position the blocking element (14) releases the locking ball (12).

6. The medical instrument according to claim 1, wherein the instrument insert (42) comprises an instrument shank (46) having a proximal end comprising a Luer connection (51).

7. The medical instrument according to claim 6, wherein the locking connection comprises a locking bolt (58) arranged on the instrument handle (1), the locking bolt being movable transversely to the longitudinal axis of the instrument shank and being releasably engageable with a recess at a proximal end of the instrument shank (46).

8. The medical instrument according to claim 7, wherein the locking bolt (58) engages behind the Luer connection (51).

9. The medical instrument according to claim 1, wherein the instrument insert (42) comprises an instrument shank (46)

which is detachably connectable to the instrument handle (1) via a locking connection (50, 40; 58).

10. The medical instrument according to claim 9, wherein the locking connection between the instrument shank (46) and the instrument handle (1) comprises a ball locking connection (50, 40).

11. The medical instrument according to claim 10, wherein the ball locking connection (50, 40) comprises a closure element (22) for securing the ball locking connection (50, 40) and a grip element (24), wherein the closure element (22) is movable into an unsecured position by movement of the grip element (24) as well as independently of movement of the grip element (24).

12. The medical instrument according to claim 10, wherein the ball locking connection (50, 40) comprises a closure sleeve (22) for securing the ball locking connection (50, 40) and a grip sleeve (24), wherein the closure sleeve (22) in a secured position blocks a movement of at least one locking ball (50) and in an unsecured position releases the locking ball (50), and wherein the closure sleeve (22) is movable into the unsecured position by movement of the grip sleeve (24) as well as independently of movement of the grip sleeve (24).

13. The medical instrument according to claim 12, wherein the closure sleeve (22) is arranged inside the grip sleeve (24) and is held in the secured position by a spring element (30), and wherein the closure sleeve (22) comprises at least one contact shoulder (32) behind which a contact shoulder (34) of the grip sleeve (24) engages only in a direction opposite to a spring force of the spring element (30).

14. The medical instrument according to claim 13, wherein the closure sleeve (22) and the grip sleeve (24) are movably guided on the instrument handle (1), and wherein the instrument handle (1) has an abutment (36) on which the grip sleeve (24) comes to bear when the closure sleeve (22) is in its secured position.

15. The medical instrument according to claim 1, wherein the blocking element partially surrounds the spring element and the cylinder sleeve surrounds the entire blocking element, the spring and at least a portion of the connection part.

16. The medical instrument according to claim 1, wherein the proximal end of the actuation rod (52) has an annular peripheral groove (54), the receiver comprising the cylinder sleeve (8) into which the proximal end of the actuation rod (52) is insertable, the cylinder sleeve (8) having at least one locking ball (12) engageable with the annular groove (54), wherein when the instrument handle is detached from the instrument insert the blocking element is pressed distally against a shoulder inside the cylinder sleeve into which a proximal end of the actuation rod is insertable, the shoulder being spaced a predetermined distance from the at least one locking ball.

17. The medical instrument according to claim 1, wherein the movable grip (4) is pivotally attached to the instrument handle (1), the movable grip being movable along an arc extending tangentially to the longitudinal axis (X) of the instrument.

* * * * *